US011013420B2

(12) United States Patent
Ravid et al.

(10) Patent No.: US 11,013,420 B2
(45) Date of Patent: May 25, 2021

(54) SYSTEMS, APPARATUSES AND METHODS FOR DETERMINING BLOOD PRESSURE

(71) Applicant: Zoll Medical Israel Ltd., Kfar Saba (IL)

(72) Inventors: Rafi Ravid, Savion (IL); Uriel Weinstein, Mazkeret Batya (IL)

(73) Assignee: ZOLL MEDICAL ISRAEL LTD., Kfar Saba (IL)

(*) Notice: Subject to any disclaimer, the term of this patent is extended or adjusted under 35 U.S.C. 154(b) by 293 days.

(21) Appl. No.: 15/117,168

(22) PCT Filed: Feb. 5, 2015

(86) PCT No.: PCT/IL2015/050140
§ 371 (c)(1),
(2) Date: Aug. 5, 2016

(87) PCT Pub. No.: WO2015/118544
PCT Pub. Date: Aug. 13, 2015

(65) Prior Publication Data
US 2016/0345845 A1  Dec. 1, 2016

Related U.S. Application Data

(60) Provisional application No. 61/935,958, filed on Feb. 5, 2014.

(51) Int. Cl.
*A61B 5/02* (2006.01)
*A61B 5/021* (2006.01)
(Continued)

(52) U.S. Cl.
CPC ......... *A61B 5/02125* (2013.01); *A61B 5/021* (2013.01); *A61B 5/0285* (2013.01);
(Continued)

(58) Field of Classification Search
CPC .. A61B 5/00; A61B 5/021; A61B 5/05; A61B 5/107
See application file for complete search history.

(56) References Cited

U.S. PATENT DOCUMENTS 4,240,445 A   12/1980   Iskander et al.
4,344,440 A   8/1982    Aaby et al.
(Continued)

FOREIGN PATENT DOCUMENTS

CN   101032400 A   9/2007
CN   101516437 A   8/2009
(Continued)

OTHER PUBLICATIONS

Tao, Teh-Ho, et al., "An Ultrawideband Radar Based Pulse Sensor for Arterial Stiffness Measurement", Proceedings of the 29th Annual International Conference of the IEEE EMBS, pp. 1679-1682, Aug. 23-26, 2007.
(Continued)

*Primary Examiner* — Ankit D Tejani
(74) *Attorney, Agent, or Firm* — Cooley LLP

(57) ABSTRACT

The present disclosure is directed to apparatuses, systems and methods for measuring time-varying radar cross section (RCS) of an artery of a patient, which may be used to determine blood pressure of a patient. In some embodiments, an apparatus is provided which comprises a radio-frequency (RF) transceiver for generating RF waves, and at least one sensor configured for positioning on or adjacent the skin of a patient, and at least one of transmitting the RF waves into tissue of the patient and receiving RF wave reflections from at least one artery located within the tissue. The apparatus may further comprise a processor having computer instructions operating thereon configured to cause the processor to determine an RF arterial pulse waveform based on the received RF wave reflections. The time-varying
(Continued)

radar cross section (RCS) comprises the RF arterial pulse waveform. This may be in turn correlated to blood pressure of the patient.

25 Claims, 5 Drawing Sheets

(51) Int. Cl.
  A61B 5/00      (2006.01)
  A61B 5/0507    (2021.01)
  A61B 5/107     (2006.01)
  A61B 5/0285    (2006.01)
  A61B 5/024     (2006.01)
  A61B 5/0456    (2006.01)

(52) U.S. Cl.
  CPC .......... *A61B 5/0507* (2013.01); *A61B 5/1075* (2013.01); *A61B 5/6804* (2013.01); *A61B 5/02416* (2013.01); *A61B 5/0456* (2013.01); *A61B 5/1076* (2013.01); *A61B 5/681* (2013.01); *A61B 5/6805* (2013.01); *A61B 5/6807* (2013.01); *A61B 5/6831* (2013.01); *A61B 5/725* (2013.01)

(56) References Cited

U.S. PATENT DOCUMENTS

| | | |
|---|---|---|
| 4,557,272 A | 12/1985 | Carr |
| 4,632,128 A | 12/1986 | Paglione et al. |
| 4,640,280 A | 2/1987 | Sterzer |
| 4,641,659 A | 2/1987 | Sepponen |
| 4,774,961 A | 10/1988 | Carr |
| 4,825,880 A | 5/1989 | Stauffer et al. |
| 4,926,868 A | 5/1990 | Larsen |
| 4,945,914 A | 8/1990 | Allen |
| 4,958,638 A | 9/1990 | Sharpe |
| 4,986,870 A | 1/1991 | Frohlich |
| 5,003,622 A | 3/1991 | Ma et al. |
| 5,109,855 A | 5/1992 | Guner |
| 5,394,882 A | 3/1995 | Mawhinney |
| 5,404,877 A | 4/1995 | Nolan |
| 5,474,574 A | 12/1995 | Payne et al. |
| 5,540,727 A | 7/1996 | Tockman et al. |
| 5,549,650 A | 8/1996 | Bornzin et al. |
| 5,668,555 A | 9/1997 | Starr |
| 5,704,355 A | 1/1998 | Bridges |
| 5,766,208 A | 6/1998 | McEwan |
| 5,807,257 A | 9/1998 | Bridges |
| 5,829,437 A | 11/1998 | Bridges |
| 5,841,288 A | 11/1998 | Meaney et al. |
| 5,865,177 A | 2/1999 | Segawa |
| 5,967,986 A | 10/1999 | Cimochowski et al. |
| 6,019,724 A | 2/2000 | Gronningsaeter et al. |
| 6,061,589 A | 5/2000 | Bridges et al. |
| 6,064,903 A | 5/2000 | Riechers et al. |
| 6,093,141 A | 7/2000 | Mosseri et al. |
| 6,144,344 A | 11/2000 | Kim |
| 6,161,036 A | 12/2000 | Matsumara et al. |
| 6,193,669 B1 | 2/2001 | Degany et al. |
| 6,208,286 B1 | 3/2001 | Rostislavovich et al. |
| 6,233,479 B1 | 5/2001 | Haddad et al. |
| 6,267,723 B1 | 7/2001 | Matsumura et al. |
| 6,330,479 B1 | 12/2001 | Stauffer |
| 6,409,662 B1 | 6/2002 | Lloyd et al. |
| 6,454,711 B1 | 9/2002 | Haddad et al. |
| 6,471,655 B1* | 10/2002 | Baura ............... A61B 5/02028 600/485 |
| 6,480,733 B1 | 11/2002 | Turcott |
| 6,526,318 B1 | 2/2003 | Ansarinia |
| 6,592,518 B2 | 7/2003 | Denker et al. |
| 6,604,404 B2 | 8/2003 | Paltieli et al. |
| 6,729,336 B2 | 5/2004 | Da Silva et al. |
| 6,730,033 B2 | 5/2004 | Yao et al. |
| 6,755,856 B2 | 6/2004 | Fierens et al. |
| 6,933,811 B2 | 8/2005 | Enokihara et al. |
| 6,940,457 B2 | 9/2005 | Lee et al. |
| 7,020,508 B2 | 3/2006 | Stivoric et al. |
| 7,122,012 B2 | 10/2006 | Bouton et al. |
| 7,130,681 B2 | 10/2006 | Gebhardt et al. |
| 7,184,824 B2 | 2/2007 | Hashimshony |
| 7,191,000 B2 | 3/2007 | Zhu et al. |
| 7,197,356 B2 | 3/2007 | Carr |
| 7,266,407 B2 | 9/2007 | Li et al. |
| 7,267,651 B2 | 9/2007 | Nelson |
| 7,272,431 B2 | 9/2007 | McGrath |
| 7,280,863 B2 | 10/2007 | Shachar |
| 7,454,242 B2 | 11/2008 | Fear et al. |
| 7,474,918 B2 | 1/2009 | Frants et al. |
| 7,479,790 B2 | 1/2009 | Choi |
| 7,493,154 B2 | 2/2009 | Bonner et al. |
| 7,529,398 B2 | 5/2009 | Zwirn et al. |
| 7,570,063 B2 | 8/2009 | Van Veen et al. |
| 7,591,792 B2 | 9/2009 | Bouton |
| 7,697,972 B2 | 4/2010 | Verard et al. |
| 7,719,280 B2 | 5/2010 | Lagae et al. |
| 7,747,302 B2 | 6/2010 | Milledge et al. |
| 7,868,627 B2 | 1/2011 | Turkovskyi |
| 8,032,211 B2 | 10/2011 | Hashimshony et al. |
| 8,211,040 B2 | 7/2012 | Kojima et al. |
| 8,295,920 B2 | 10/2012 | Bouton et al. |
| 8,352,015 B2 | 1/2013 | Bernstein et al. |
| 8,473,054 B2 | 6/2013 | Pillai et al. |
| 8,682,399 B2 | 3/2014 | Rabu |
| 8,882,759 B2 | 11/2014 | Manley et al. |
| 8,938,292 B2 | 1/2015 | Hettrick et al. |
| 8,983,592 B2 | 3/2015 | Belalcazar |
| 8,989,837 B2 | 3/2015 | Weinstein et al. |
| 9,220,420 B2 | 12/2015 | Weinstein et al. |
| 9,265,438 B2 | 2/2016 | Weinstein et al. |
| 9,572,512 B2 | 2/2017 | Weinstein et al. |
| 9,629,561 B2 | 4/2017 | Weinstein et al. |
| 9,788,752 B2 | 10/2017 | Weinstein et al. |
| 10,136,833 B2 | 11/2018 | Weinstein et al. |
| 10,548,485 B2 | 2/2020 | Arditi et al. |
| 10,588,599 B2 | 3/2020 | Weinstein et al. |
| 10,680,324 B2 | 6/2020 | Weinstein et al. |
| 2002/0032386 A1 | 3/2002 | Sackner et al. |
| 2002/0045836 A1 | 4/2002 | Alkawwas |
| 2002/0049394 A1 | 4/2002 | Roy et al. |
| 2002/0050954 A1 | 5/2002 | Jeong-Kun et al. |
| 2002/0147405 A1 | 10/2002 | Denker et al. |
| 2002/0151816 A1 | 10/2002 | Rich et al. |
| 2003/0036674 A1 | 2/2003 | Bouton |
| 2003/0036713 A1 | 2/2003 | Bouton et al. |
| 2003/0088180 A1 | 5/2003 | Van Veen et al. |
| 2003/0100815 A1 | 5/2003 | Da Silva et al. |
| 2003/0199770 A1 | 10/2003 | Chen et al. |
| 2003/0219598 A1 | 11/2003 | Sakurai |
| 2004/0015087 A1 | 1/2004 | Boric-Lubecke et al. |
| 2004/0073081 A1 | 4/2004 | Schramm |
| 2004/0077943 A1 | 4/2004 | Meaney et al. |
| 2004/0077952 A1 | 4/2004 | Rafter et al. |
| 2004/0249257 A1 | 12/2004 | Tupin et al. |
| 2004/0254457 A1 | 12/2004 | van der Weide |
| 2004/0261721 A1 | 12/2004 | Steger |
| 2005/0038503 A1 | 2/2005 | Greenhalgh et al. |
| 2005/0107693 A1 | 5/2005 | Fear et al. |
| 2005/0192488 A1 | 9/2005 | Bryenton |
| 2005/0245816 A1 | 11/2005 | Candidus et al. |
| 2006/0004269 A9 | 1/2006 | Caduff et al. |
| 2006/0009813 A1 | 1/2006 | Taylor et al. |
| 2006/0025661 A1 | 2/2006 | Sweeney et al. |
| 2006/0101917 A1 | 5/2006 | Merkel |
| 2006/0237223 A1 | 10/2006 | Chen et al. |
| 2006/0265034 A1 | 11/2006 | Aknine et al. |
| 2007/0016032 A1 | 1/2007 | Aknine |
| 2007/0016050 A1 | 1/2007 | Moehring et al. |
| 2007/0055123 A1 | 3/2007 | Takiguchi |
| 2007/0100385 A1 | 5/2007 | Rawat |
| 2007/0123770 A1 | 5/2007 | Bouton et al. |
| 2007/0123778 A1 | 5/2007 | Kantorovich |
| 2007/0135721 A1 | 6/2007 | Zdeblick |

(56) References Cited

U.S. PATENT DOCUMENTS

| | | |
|---|---|---|
| 2007/0152812 A1 | 7/2007 | Wong et al. |
| 2007/0156057 A1 | 7/2007 | Cho et al. |
| 2007/0162090 A1 | 7/2007 | Penner |
| 2007/0191733 A1 | 8/2007 | Gianchandani et al. |
| 2007/0263907 A1 | 11/2007 | McMakin et al. |
| 2008/0027313 A1 | 1/2008 | Shachar |
| 2008/0030284 A1 | 2/2008 | Tanaka et al. |
| 2008/0036668 A1 | 2/2008 | White et al. |
| 2008/0097199 A1 | 4/2008 | Mullen |
| 2008/0129511 A1 | 6/2008 | Yuen et al. |
| 2008/0139934 A1 | 6/2008 | McMorrow et al. |
| 2008/0167566 A1 | 7/2008 | Univer et al. |
| 2008/0169961 A1 | 7/2008 | Steinway et al. |
| 2008/0183247 A1 | 7/2008 | Harding |
| 2008/0200802 A1 | 8/2008 | Bahavaraju et al. |
| 2008/0224688 A1 | 9/2008 | Rubinsky et al. |
| 2008/0269589 A1 | 10/2008 | Thijs et al. |
| 2008/0283282 A1 | 11/2008 | Kawasaki et al. |
| 2008/0294036 A1 | 11/2008 | Hoi et al. |
| 2008/0316124 A1 | 12/2008 | Hook |
| 2008/0319301 A1 | 12/2008 | Busse |
| 2009/0021720 A1 | 1/2009 | Hecker |
| 2009/0048500 A1 | 2/2009 | Corn |
| 2009/0076350 A1 | 3/2009 | Bly et al. |
| 2009/0153412 A1 | 6/2009 | Chiang et al. |
| 2009/0153433 A1 | 6/2009 | Nagai et al. |
| 2009/0187109 A1 | 7/2009 | Hashimshony |
| 2009/0203972 A1 | 8/2009 | Heneghan et al. |
| 2009/0227882 A1 | 9/2009 | Foo |
| 2009/0240132 A1 | 9/2009 | Friedman |
| 2009/0240133 A1 | 9/2009 | Friedman et al. |
| 2009/0248450 A1 | 10/2009 | Fernandez |
| 2009/0262028 A1 | 10/2009 | Mumbru et al. |
| 2009/0281412 A1 | 11/2009 | Boyden et al. |
| 2009/0299175 A1 | 12/2009 | Bernstein et al. |
| 2009/0312615 A1 | 12/2009 | Caduff et al. |
| 2009/0322636 A1 | 12/2009 | Brigham et al. |
| 2010/0004517 A1* | 1/2010 | Bryenton ............ A61B 5/02055 600/301 |
| 2010/0013318 A1 | 1/2010 | Iguchi et al. |
| 2010/0052992 A1 | 3/2010 | Okamura et al. |
| 2010/0056907 A1 | 3/2010 | Rappaport et al. |
| 2010/0076315 A1 | 3/2010 | Erkamp et al. |
| 2010/0081895 A1 | 4/2010 | Zand |
| 2010/0106223 A1 | 4/2010 | Grevious |
| 2010/0152600 A1 | 6/2010 | Droitcour et al. |
| 2010/0256462 A1 | 10/2010 | Rappaport et al. |
| 2010/0265159 A1 | 10/2010 | Ando et al. |
| 2010/0305460 A1* | 12/2010 | Pinter ................. A61B 5/0507 600/509 |
| 2010/0312301 A1 | 12/2010 | Stahmann |
| 2010/0321253 A1 | 12/2010 | Ayala Vazquez et al. |
| 2010/0332173 A1 | 12/2010 | Watson et al. |
| 2011/0004076 A1 | 1/2011 | Janna et al. |
| 2011/0009754 A1 | 1/2011 | Wenzel et al. |
| 2011/0022325 A1 | 1/2011 | Craddock et al. |
| 2011/0040176 A1 | 2/2011 | Razansky et al. |
| 2011/0060215 A1 | 3/2011 | Tupin et al. |
| 2011/0068995 A1 | 3/2011 | Baliarda et al. |
| 2011/0125207 A1 | 5/2011 | Nabutovsky et al. |
| 2011/0130800 A1 | 6/2011 | Weinstein et al. |
| 2011/0257555 A1 | 10/2011 | Banet et al. |
| 2012/0029323 A1 | 2/2012 | Zhao |
| 2012/0065514 A1 | 3/2012 | Naghavi et al. |
| 2012/0068906 A1 | 3/2012 | Asher et al. |
| 2012/0098706 A1 | 4/2012 | Lin et al. |
| 2012/0104103 A1 | 5/2012 | Manzi |
| 2012/0330151 A1 | 12/2012 | Weinstein et al. |
| 2013/0041268 A1 | 2/2013 | Rimoldi et al. |
| 2013/0053671 A1 | 2/2013 | Farra |
| 2013/0069780 A1 | 3/2013 | Tran et al. |
| 2013/0090566 A1 | 4/2013 | Mühlsteff et al. |
| 2013/0123614 A1 | 5/2013 | Bernstein et al. |
| 2013/0184573 A1 | 7/2013 | Pahlevan et al. |
| 2013/0190646 A1 | 7/2013 | Weinstein et al. |
| 2013/0225989 A1 | 8/2013 | Saroka et al. |
| 2013/0231550 A1 | 9/2013 | Weinstein et al. |
| 2013/0297344 A1 | 11/2013 | Cosentino et al. |
| 2013/0310700 A1 | 11/2013 | Wiard et al. |
| 2014/0046690 A1 | 2/2014 | Gunderson et al. |
| 2014/0081159 A1 | 3/2014 | Tao et al. |
| 2014/0128032 A1 | 5/2014 | Muthukumar |
| 2014/0163425 A1 | 6/2014 | Tran |
| 2014/0288436 A1 | 9/2014 | Venkatraman et al. |
| 2015/0018676 A1† | 1/2015 | Barak |
| 2015/0025333 A1 | 1/2015 | Weinstein et al. |
| 2015/0150477 A1 | 6/2015 | Weinstein et al. |
| 2015/0164349 A1 | 6/2015 | Gopalakrishnan et al. |
| 2015/0335310 A1 | 11/2015 | Bernstein et al. |
| 2016/0073924 A1 | 3/2016 | Weinstein et al. |
| 2016/0198957 A1 | 7/2016 | Arditi et al. |
| 2016/0198976 A1 | 7/2016 | Weinstein et al. |
| 2016/0213321 A1 | 7/2016 | Weinstein et al. |
| 2016/0317054 A1 | 11/2016 | Weinstein et al. |
| 2017/0035327 A1 | 2/2017 | Yuen et al. |
| 2017/0065184 A1† | 3/2017 | Barak |
| 2017/0135598 A1 | 5/2017 | Weinstein et al. |
| 2017/0229763 A1† | 8/2017 | Barak |
| 2017/0238966 A1 | 8/2017 | Weinstein et al. |
| 2017/0296093 A1 | 10/2017 | Weinstein et al. |
| 2019/0046038 A1 | 2/2019 | Weinstein et al. |
| 2019/0298208 A1 | 10/2019 | Weinstein et al. |
| 2020/0113447 A1 | 4/2020 | Arditi et al. |

FOREIGN PATENT DOCUMENTS

| | | |
|---|---|---|
| DE | 10008886 | 9/2001 |
| EP | 1834588 A1 | 9/2007 |
| EP | 2506917 A1 | 10/2012 |
| EP | 2 602 870 A1 | 6/2013 |
| JP | 05-038957 | 5/1993 |
| JP | 10-137193 A | 5/1998 |
| JP | 2000-235006 A | 8/2000 |
| JP | 2001-525925 A | 12/2001 |
| JP | 2002-094321 | 3/2002 |
| JP | 2003-141466 | 5/2003 |
| JP | 2004-526488 A | 9/2004 |
| JP | 2006-208070 A | 8/2006 |
| JP | 2006-319767 A | 11/2006 |
| JP | 2007-061359 A | 3/2007 |
| JP | 2007-149959 | 6/2007 |
| JP | 2008-515548 A | 5/2008 |
| JP | 2008-148141 A | 6/2008 |
| JP | 2008-518706 A | 6/2008 |
| JP | 2008-530546 A | 7/2008 |
| JP | 2008-542759 A | 11/2008 |
| JP | 2008-545471 | 12/2008 |
| JP | 2009-514619 A | 4/2009 |
| JP | 2009-522034 A | 6/2009 |
| JP | 2010-507929 | 3/2010 |
| JP | 2010-072957 | 4/2010 |
| JP | 2010-512190 A | 4/2010 |
| JP | 2010-530769 | 9/2010 |
| JP | 2010-537766 A | 12/2010 |
| JP | 2011-507583 A | 3/2011 |
| JP | 2011-524213 A | 9/2011 |
| JP | 2012-090257 | 5/2012 |
| WO | WO 02/03499 A1 | 1/2002 |
| WO | WO 2003/009752 A2 | 2/2003 |
| WO | WO 2006/127719 A2 | 11/2006 |
| WO | WO 2006/130798 A2 | 12/2006 |
| WO | WO 2007/017861 A2 | 2/2007 |
| WO | WO 2007/023426 A2 | 3/2007 |
| WO | WO 2008/070856 A2 | 6/2008 |
| WO | WO 2008/148040 A1 | 12/2008 |
| WO | WO 2009/031149 A2 | 3/2009 |
| WO | WO 2009/031150 A2 | 3/2009 |
| WO | WO 2009/060182 A1 | 5/2009 |
| WO | WO 2009/081331 A1 | 7/2009 |
| WO | WO 2009/152625 A1 | 12/2009 |
| WO | WO 2011/067623 A1 | 6/2011 |
| WO | WO 2011/067685 A1 | 6/2011 |
| WO | WO 2011/141915 A2 | 11/2011 |
| WO | WO 2012/011065 A1 | 1/2012 |

(56) References Cited

FOREIGN PATENT DOCUMENTS

| WO | WO 2012/011066 A1 | 1/2012 |
|---|---|---|
| WO | WO 2013/118121 A1 | 8/2013 |
| WO | WO 2013/121290 A2 | 8/2013 |
| WO | WO 2015/118544 A1 | 8/2015 |

OTHER PUBLICATIONS

International Search Report and Written Opinion, dated Jun. 24, 2015 for PCT/IL2015/050140, filed Feb. 5, 2015.
Alekseev, S. I., et al. "Human Skin permittivity determined by millimeter wave reflection measurements", Bioelectromagnetics, vol. 28, No. 5, Jul. 1, 2007, pp. 331-339.
Ascension Technology Corporation, "TrakSTAR Adds Versatility to Ascension's New Product Line: Desktop Model Joins driveBAY Tracker for Fast Guidance of Miniaturized Sensor", USA, Apr. 7, 2008.
Bell et al., "A Low-Profile Achimedean Spiral Antenna Using an EBG Ground Plane", IEEE Antennas and Wireless Propagation Letters 3, pp. 223-226 (2004).
Beyer-Enke et al., Intra-arterial Doppler flowmetry in the superficial femoral artery following angioplasty., 2000, European Radiology, vol. 10, No. 4, p. 642-649.
Claron Technology Inc., "MicronTracker 3: A New Generation of Optical Trackers", Canada, 2009.
Czum et al., "The Vascular Diagnostic Laboratory", The Heart & Vascular Institute Newsletter, vol. 1, USA, Winter, 2001.
Extended Search Report for European Application No. 11809360.8, dated Mar. 11, 2014.
Ghosh, et al., Immediate Evaluation of Angioplasty and Stenting Results in Supra-Aortic Arteries by Use of a Doppler-Tipped Guidewire, Aug. 2004, American Journal of Neuroradiology, vol. 25, p. 1172-1176.
Gentili et al., "A Versatile Microwave Plethysmograph for the Monitoring of Physiological Parameters", IEEE Transactions on Biomedical Engineering, IEEE Service Center, Pitscataway, NJ, US, vol. 49, No. 10, Oct. 1, 2002.
Haude et al., Intracoronary Doppler- and Quantitative Coronary Angiography-Derived Predictors of Major Adverse Cardiac Events After Stent Implantation, Mar. 6, 2001, Circulation, vol. 103(9), p. 1212-1217.
Immersion Corporation, "Immersion Introduces New 3D Digitizing Product—MicroScribe G2; Faster Data Transfer, USB Compatibility, New Industrial Design", Press Release, San Jose, USA, Jul. 1, 2002.
International Preliminary Report on Patentability, dated Jan. 31, 2013, for International Application No. PCT/IB2011/053246, 22 pages.
International Preliminary Report on Patentability, dated Aug. 19, 2014 for International Application No. PCT/IB2013/000663 filed Feb. 15, 2013.
International Preliminary Report on Patentability, dated Jun. 5, 2012, for International Application No. PCT/IB2010/054861.
International Preliminary Report on Patentability, dated Jan. 22, 2013, for International Application No. PCT/IB2011/053244, 6 pages.
International Preliminary Report on Patentability, dated Jun. 5, 2012, for International Application No. PCT/IB2009/055438.
International Search Report and Written Opinion of the International Searching Authority, dated Dec. 2, 2011, for International Application No. PCT/IB2011/053244, 7 pages.
International Search Report and Written Opinion, dated Dec. 13, 2011, for International Application No. PCT/IB2011/053246, 24 pages.
International Search Report and Written Opinion, dated Feb. 26, 2015, for International Application No. PCT/IL2014/050937.
International Search Report and Written Opinion, dated Jul. 20, 2010, for International Application No. PCT/IB2009/055438.

International Search Report and Written Opinion, dated Nov. 26, 2013 for International Application No. PCT/IB2013/000663 filed Feb. 15, 2013.
International Search Report, dated Apr. 5, 2011, for International Application No. PCT/IB2010/054861.
International Search Report and Written Opinion, dated Nov. 28, 2018 for International Application No. PCT/IL2018/050808 filed Jul. 20, 2018.
Kantarci et al., Follow-Up of Extracranial Vertebral Artery Stents with Doppler Sonography., Sep. 2006, American Journal of Roentgenology, vol. 187, p. 779-787.
Lal et al., "Duplex ultrasound velocity criteria for the stented carotid artery", Journal of Vascular Surgery, vol. 47, No. 1, pp. 63-73, Jan. 2008.
Larsson et al., "State Diagrams of the Heart—a New Approach to Describing Cardiac Mechanics", Cardiovascular Ultrasound 7:22 (2009).
Liang, Jing et al., Microstrip Patch Antennas on Tunable Electromagnetic Band-Gap Substrates, IEEE Transactions on Antennas and Propagation, vol. 57, No. 6, Jun. 2009.
Lin, J.C. et al., "Microwave Imaging of Cerebral Edema", Proceedings of the IEEE, IEEE, NY, US, vol. 70, No. 5; May 1, 1982, pp. 523-524.
Miura et al. "Time Domain Reflectometry: Measurement of Free Water in Normal Lung and Pulmonary Edema," American Journal of Physiology—Lung Physiology 276:1 (1999), pp. L207-L212.
Notice of Reasons for Rejection, dated Apr. 17, 2015, for JP 2013-520273.
Notice of Reasons for Rejection, dated Apr. 28, 2014, for JP 2012-541588.
Notice of Reasons for Rejection, dated Mar. 31, 2015, for JP 2012-541588.
Partial Supplementary Search Report, dated Oct. 19, 2015, for EP Application No. 13748671.8.
Paulson, Christine N., et al. "Ultra-wideband radar methods and techniques of medical sensing and imaging" Proceedings of Spie, vol. 6007, Nov. 9, 2005, p. 60070L.
Pedersen, P.C., et al., "Microwave Reflection and Transmission Measurements for Pulmonary Diagnosis and Monitoring", IEEE Transactions on Biomedical Engineering, IEEE Service Center, Piscataway, NJ, US, vol. BME-19, No. 1, Jan. 1, 1978; pp. 40-48.
Polhemus, "Fastrak: The Fast and Easy Digital Tracker", USA, 2008.
Ringer et al., Follow-up of Stented Carotid Arteries by Doppler Ultrasound, Sep. 2002, Neurosurgery, vol. 51, No. 3, p. 639-643.
Supplementary European Search Report and European Search Opinion, dated Jun. 13, 2013, for European Application No. 09851811.1.
Supplementary European Search Report and European Search Opinion, dated Mar. 11, 2014, for European Application No. 11809359.1.
Supplementary European Search Report and Search Opinion, dated Dec. 4, 2014, for EP Application No. 10834292.4.
Supplementary European Search Report, dated Mar. 7, 2016, for Ep Application No. 13748671.8.
Written Opinion for International Application No. PCT/IB2010/054861 dated Apr. 5, 2011.
Yang, F. et al. "Enhancement of Printed Dipole Antennas Characteristics Using Semi-EBG Ground Plane", Journal of Electromagnetic Waves and Application, U.S., Taylor & Francis, Apr. 3, 2006, vol. 8, pp. 993-1006.
Lin et al., "Enhanced performances of a compact conical pattern annular-ring patch antenna using a slotted ground plane," Microwave Conference, 2001. APMC 2001. 2001 Asia-Pacific Dec. 3-6, 201, IEEE, vol. 3, Dec. 3, 2001, pp. 1036-1039.
Lin et al: "Using dual-antenna nanosecond pulse near field sensing technology for non-contact and continuous blood pressure measurement", Engineering in Medicine and Biology Society (EMBC), 2013 35th Annual International Conference of the IEEE, IEEE, Aug. 28, 2012 (Aug. 28, 2012), pp. 219-222.
Matsugatani et al., "Surface Wave Distribution Over Electromagnetic Bandgap (EBG) and EBG Reflective Shield for Patch Antenna," IEICE Transactions on Electronics, vol. E88-C, No. 12, Dec. 1, 2005, pp. 2341-2349.

(56) References Cited

OTHER PUBLICATIONS

Solberg et al: "A feasibility study on aortic pressure estimation using UWB radar", Ultra-Wideband, 2009. ICUWB 2009. IEEE International Conference on, IEEE, Piscataway, NJ, USA, Sep. 9, 2009 (Sep. 9, 2009), pp. 464-468.
Yang et al., "Reflection phase characterizations of the EBG ground plane for low profile wire antenna applications," IEEE Transactions on Antennas and Propagation, vol. 51, No. 10, Oct. 1, 2003, pp. 2691-2703.
Zhang et al., "Planar artificial magnetic conductors and patch antennas," IEEE Transactions on Antennas and Propagation, vol. 51, No. 10, Oct. 1, 2003, pp. 2704-2712.
Barak, U.S. Appl. No. 62/024,403, filed Mar. 9, 2017.†

\* cited by examiner
† cited by third party

SYSTEMS, APPARATUSES AND METHODS FOR DETERMINING BLOOD PRESSURE

CROSS-REFERENCE TO RELATED APPLICATIONS

This application is a 371 National Stage application of PCT Application No. PCT/IL2015/050140, filed Feb. 5, 2015, titled "Systems, Apparatuses and Methods for Determining Blood Pressure," which in turn is a non-provisional of and claims priority under 35 USC § 119 to: U.S. provisional patent application Ser. No. 61/935,958, filed Feb. 5, 2014, entitled "Systems and Methods for Determining Blood Pressure Using Electromagnetic Waves." Both disclosures are herein incorporated by reference in their entireties.

FIELD OF THE DISCLOSURE

Embodiments of the current disclosure are directed toward blood pressure measurement, and more particularly, systems and methods for blood pressure measurement utilizing electromagnetic radiation/waves.

BACKGROUND OF THE DISCLOSURE

Radio-frequency (RF) electromagnetic radiation has been used for diagnosis and imaging of body tissues, examples of which may be found in PCT publication no. WO2011/067623, US publication nos. 2009/0299175 and 2009/0240133, and U.S. Pat. Nos. 4,926,868 and 5,766,208.

WO 2011/067623 is understood to be directed to a diagnostic apparatus that includes an antenna, which directs RF electromagnetic waves into a living body and generates signals responsively to the waves that are scattered from within the body. US patent publication no. 2009/0240133 is understood to be directed to a radio apparatus and method for non-invasive, thoracic radio interrogation of a subject for the collection of hemodynamic, respiratory and/or other cardiopulmonary related data. US patent publication no. 2009/0299175, is understood to be directed to a method and apparatus for determining and tracking the location of a metallic object in a living body, using a radar detector adapted to operate on a living body. U.S. Pat. No. 4,926,868 is understood to be directed to a method and apparatus for cardiac hemodynamic monitoring based on the complex field amplitudes of microwaves propagated through and scattered by thoracic cardiovascular structures, particularly the heart chambers, as a function of time during the cardiac cycle.

However, none of these references are understood to disclose ascertaining blood pressure utilizing radio-frequency (RF) waves.

SUMMARY OF SOME OF THE EMBODIMENTS

Embodiments of the present disclosure present methods, systems and apparatuses techniques for continuous Non-Invasive Blood Pressure (cNIBP) measurement are discussed in the present disclosure (in some embodiments, such measurements may be non-continuous). In such embodiments, cNIBP measurements may be accomplished by determining, for example, Pulse Wave Velocity (PWV), which can be used as, for example, a measure of arterial stiffness. In some instances, PWV corresponds to the velocity of propagation of the arterial pressure pulse between points along the arterial tree, which may depend on, amongst other things, the blood pressure. Accordingly, determination of PWV and/or the pulse transit time (PTT) between points along the arterial tree may provide information on the blood pressure in the arteries.

In some embodiments, one or more sensors may be used to determine the PTT, and/or the pulse wave arrival time, which may also be referred to as the pulse arrival time (PAT), which may be different from the PTT. For example, there may be a delay between the generation of the pulse by the ventricular muscle and the opening of the aortic valve. In some instances, when using sensors such as an electrocardiogram (ECG) device and a photo-plethysmograph (PPG), the PAT may correspond to the delay between the ECG's QRS peak (e.g., R-peak) and a point on the PPG signal representing the pressure pulse at a peripheral artery. Examples of such sensors comprise ECGs, PPGs, radio-frequency (RF) sensors, etc. In some embodiments, the RF sensor allows for determination/estimation of the arterial pulse waveform which may provide clinical information such as, but not limited to, arterial stiffness, PWV, cardiac output, cNIBP measurements, etc.

In some embodiments, an apparatus and a method for measuring time-varying radar cross section (RCS) of an artery of a patient are disclosed. The apparatus comprises a RF transceiver for generating RF waves, at least one sensor configured for positioning on or adjacent the skin of a patient, and at least one of transmitting the RF waves into tissue of the patient and receiving RF wave reflections from at least one artery located within the tissue. In some implementations, the at least one sensor comprises at least one antennae. In some instances, it may be configured with flexibility that allows the sensor to conform to the skin of the patient. The apparatus also comprises a processor having computer instructions operating thereon configured to cause the processor to execute some or all steps of the method disclosed herein. The steps of the method comprise determining an RF arterial pulse waveform based on the received RF wave reflections, where the time-varying RCS comprises the RF arterial pulse waveform.

In some embodiments, the method also comprises the steps of correlating the time-varying RCS to a time-varying diameter of the at least one artery, conditioning the RF arterial pulse waveform using at least one radar echo from a specific range, and adapting the specific range to the at least one artery. In some implementations, the steps also include conditioning the RF arterial pulse waveform using band pass filtering, and determining a time location of at least one of a peak of the RF arterial pulse waveform, the first derivative peak, and other points marking an RF-arterial-pulse-arrive-time (RE-PAT). In some embodiments, the methods include the steps of characterizing the RF arterial pulse waveform. For example, characterizing may comprise determining a timing of the dicrotic notch of the waveform.

In some embodiments, the apparatus comprises an ECG sensor configured for positioning on the body of the patient for receiving signals corresponding to an ECG waveform, where signals from the ECG sensor are synchronized with the RF wave reflections. In some instances, the method includes determining arterial-pulse-arrival-time (PAT) based on a time difference between the RF-PAT and an R-peak of the ECG waveform. The apparatus may also comprise an ECG sensor configured for positioning on the body of the patient for receiving signals corresponding to an ECG waveform. Further, the apparatus may include the at least one sensor positioned to receive RF wave reflections from the aorta of the patient, where signals from the ECG sensor are synchronized with the RF wave reflections. In some instances, the method may comprise the step of determining an R-peak of the ECG waveform, and determining a time difference between the RF-arterial-pulse-arrival-time (RF-PAT) and the R-peak to determine a pre-ejection period (PEP). In addition, the computer instructions may be further configured to cause the processor to determine PTT, where PTT is determined by subtracting PEP from PAT.

In some embodiments, the at least one sensor may be configured for sensing RF wave reflections corresponding to PAT to each of two different arterial tree locations. In some instances, the method includes the step of determining the PAT at each location and determining the difference between the PAT at the two locations so as to determine a PTT. The two different arterial tree locations may be discerned based on depth resolution of the tissue. In some embodiments, the apparatus may comprise a second sensor, where the first sensor is configured for sensing RF wave reflections corresponding to PAT at a first arterial tree location, and where the second sensor is configured for sensing signals corresponding to PAT at a second arterial tree location. In some embodiments, the method includes determining the PAT at each location and determining the difference between the PAT at the two locations so as to determine the PTT. In such embodiments, the first arterial tree location and the second arterial tree location comprise different locations on the same arterial tree. In some instances, the first arterial tree location and the second arterial tree location comprise different arterial trees. In some instances, the first arterial tree location and the second arterial tree location may comprise different arterial trees on different areas of the body of a patient.

In some embodiments, the method comprises the step of utilizing an EGG waveform of the patient to synchronize the first and second sensors. Further, it includes gating the time measurement between the first and second sensors, where one sensor gates the measurement of the other.

In some of the embodiments disclosed above, the second sensor comprises a photo-plethysmograph (PPG) sensor or an RF sensor. In addition, the method includes the step of determining the patient's blood pressure as a function of PTT, where parameters used to determine NT are calibrated for the patient. In some embodiments, the method includes determining arterial PWV, where PWV equals the propagation distance of the arterial pulse wave divided by PTT.

It should be appreciated that all combinations of the foregoing concepts and additional concepts discussed in greater detail below (provided such concepts are not mutually inconsistent) are contemplated as being part of the inventive subject matter disclosed herein. In particular, all combinations of claimed subject matter appearing at the end of this disclosure are contemplated as being part of the inventive subject matter disclosed herein. It should also be appreciated that terminology explicitly employed herein that also may appear in any disclosure incorporated by reference should be accorded a meaning most consistent with the particular concepts disclosed herein.

BRIEF DESCRIPTION OF THE DRAWINGS

The skilled artisan will understand that the drawings primarily are for illustrative purposes and are not intended to limit the scope of the inventive subject matter described herein. The drawings are not necessarily to scale; in some instances, various aspects of the inventive subject matter disclosed herein may be shown exaggerated or enlarged in the drawings to facilitate an understanding of different features. In the drawings, like reference characters generally refer to like features (e.g., functionally similar and/or structurally similar elements).

DETAILED DESCRIPTION OF SOME OF THE EMBODIMENTS

In some embodiments of the present disclosure, systems and methods for determining blood pressure using electromagnetic waves are presented. For example, RF sensors (e.g., antenna) may be utilized to receive and/or transmit RF signals. In some instances, the RF signal waveform can be continuous or based on step frequency. In some implementations, the signals may have a wide range of frequencies, for example, the RF frequency may range from about 300 MHz to about 3 GHz. In some embodiments, the RF sensor can achieve a range (e.g., depth) resolution that allows filtering of reflections from relevant depth in a patient's body. For example, the sensor may allow penetration of a few centimeters into the body, facilitating its usage for a variety of arteries (e.g. anterior tibial, popliteal, brachial, carotid, etc.).

In some implementations, the RF sensors may be used in conjunction with other sensors/devices, such as (for example) an ECG sensor/device and/or a PPG sensor, to determine PTT and/or PAT of a pulse wave in an artery. In some embodiments, there may be a time lapse between the ventricular polarization and the opening of the aortic valve—i.e., the Pre-Ejection Period (PEP)—which, in some embodiments, corresponds to the time it takes for the myocardium to raise sufficient pressure to open the aortic valve and start pushing blood out of the ventricle. In some instances, the effects of the PEP may be significant in determining blood pressure levels.

In some embodiments, the PTT to some point along the arterial tree (e.g., peripheral location in the arterial system) may be represented as the difference between the arrival time of the pulse at the point and the pre-ejection period, i.e., PTT=PAT−PEP. Upon determining or estimating the PTT, in some embodiments, the PWV may then be calculated based on the distance the pulse traveled to arrive at the point and the estimated/determined PTT. In some implementations, blood pressure values such as systolic and/or diastolic values can be determined non-invasively from the PWV and/or the PTT. For example, linear transformations relating the systolic blood pressure (SBP) and diastolic blood pressure (DBP) to the PTT may be expressed as follow:

$$SBP=(a \times PTT)+b,$$

$$DBP=(c \times PTT)+d,$$

where the coefficients a, b, c and d can be calibrated for each patient. In some embodiments, other types of transformations may be used to calculate blood pressures. For example, for a model that assumes constant artery thickness and radius, blood pressure P may be expressed as $P=a\times\ln(PTT)+b$, where, again a and b are constants to be calibrated for each patient. In any case, in some embodiments, obtaining PTT, or conversely PWV of a pulse in an artery, may lead to the determination of blood pressure levels in the artery.

Usage of an RF Sensor and an ECG for Determining PEP Correction

Figure 1A:
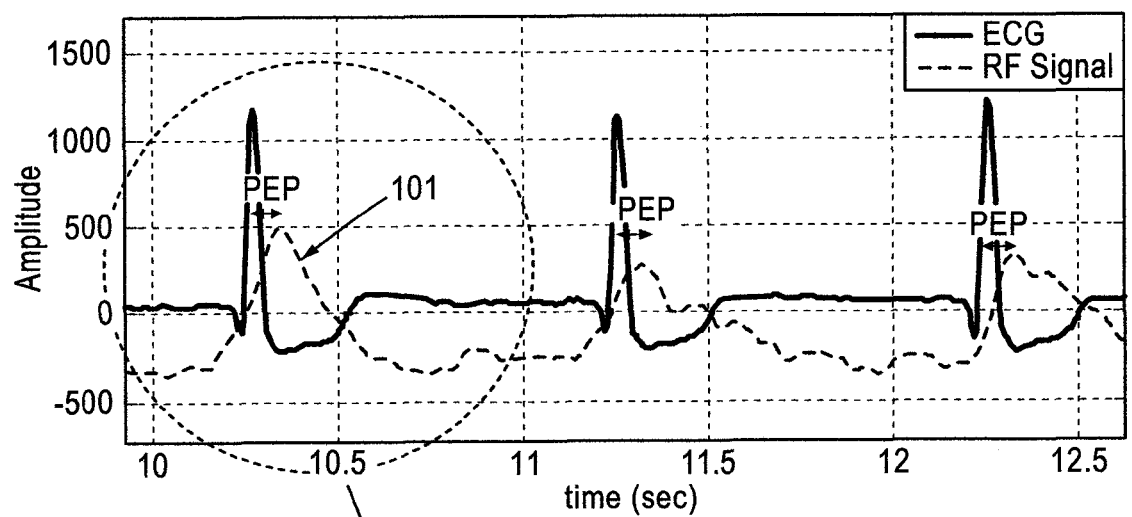
FIGS. 1A-B shows an example embodiment of determination of the pre-ejection period (PEP) from electrocardiogram and radio-frequency signal measurements.
Figure 1B:
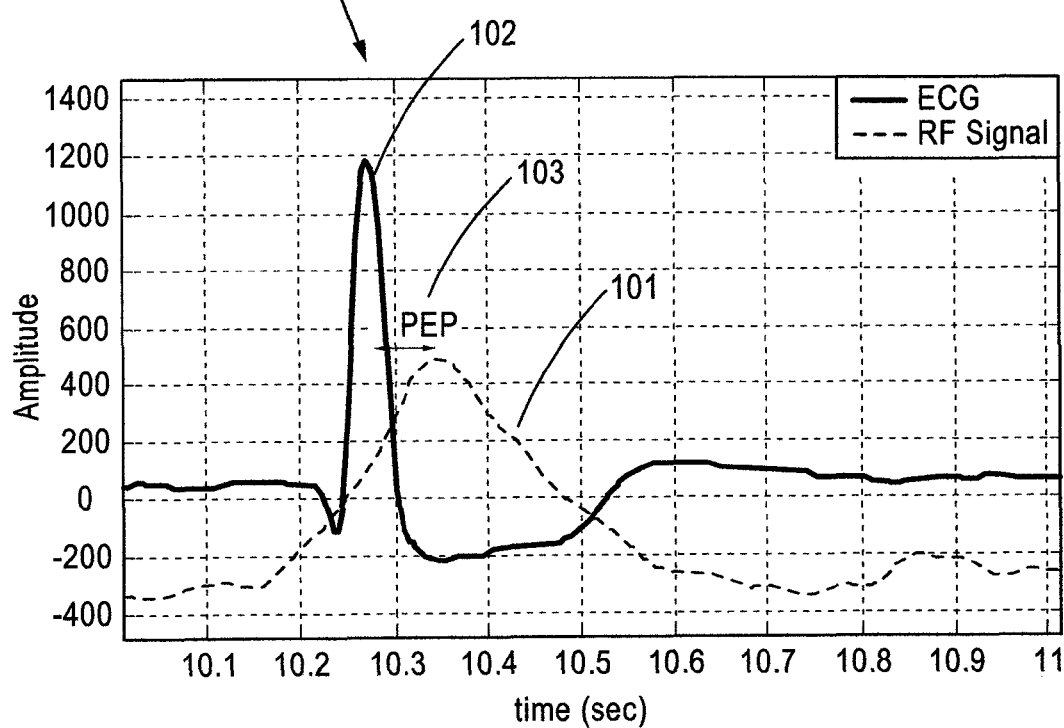

In some embodiments, RF waves may be used to locate the time of the opening of the aortic valve. For example, the reflected electromagnetic signal (with sensors located in the appropriate place, and optionally after appropriate filtering) may provide information on the opening of the aortic valve, and hence can be used in conjunction with the ECG signals that represent the activation of the ventricles, for determining the PEP. Once PEP is obtained, in some embodiments, the calculation of the PTT follows from the relation PTT=PAT–PEP upon finding PAT. In some instances, PAT can be found by comparing the simultaneous detection of ECG signals to that of the PPG signals, which represent the activation of the pulses at the ventricles and arrival of the pulses at the peripheral arteries, respectively. For example, the comparison may correspond to the delay between the ECG's QRS peak (i.e., R-peak) and a point on the PPG signal representing the pressure pulse at a peripheral artery. In such embodiments, one or more PPG sensors may be located near a peripheral artery (e.g., finger, ear-lobe, etc.), and one or more RF sensors (e.g., antenna) may be located so that the antennae receives reflections from the heart, for example, at the sternum. The heart signals can be isolated by a combination of range and Doppler filtering of the RF signals. For example, the RF signal may be filtered to isolate heart reflections from the relevant depth, and may also be filtered to remove reflections from static objects. As to the ECG signals, the R-peak time may be determined from the ECG signals. FIG. 1 shows an example embodiment of PEP correction estimation 103 from the time difference between the ECG R-peak 102 and the RF signal pulse 101.

Figure 2:
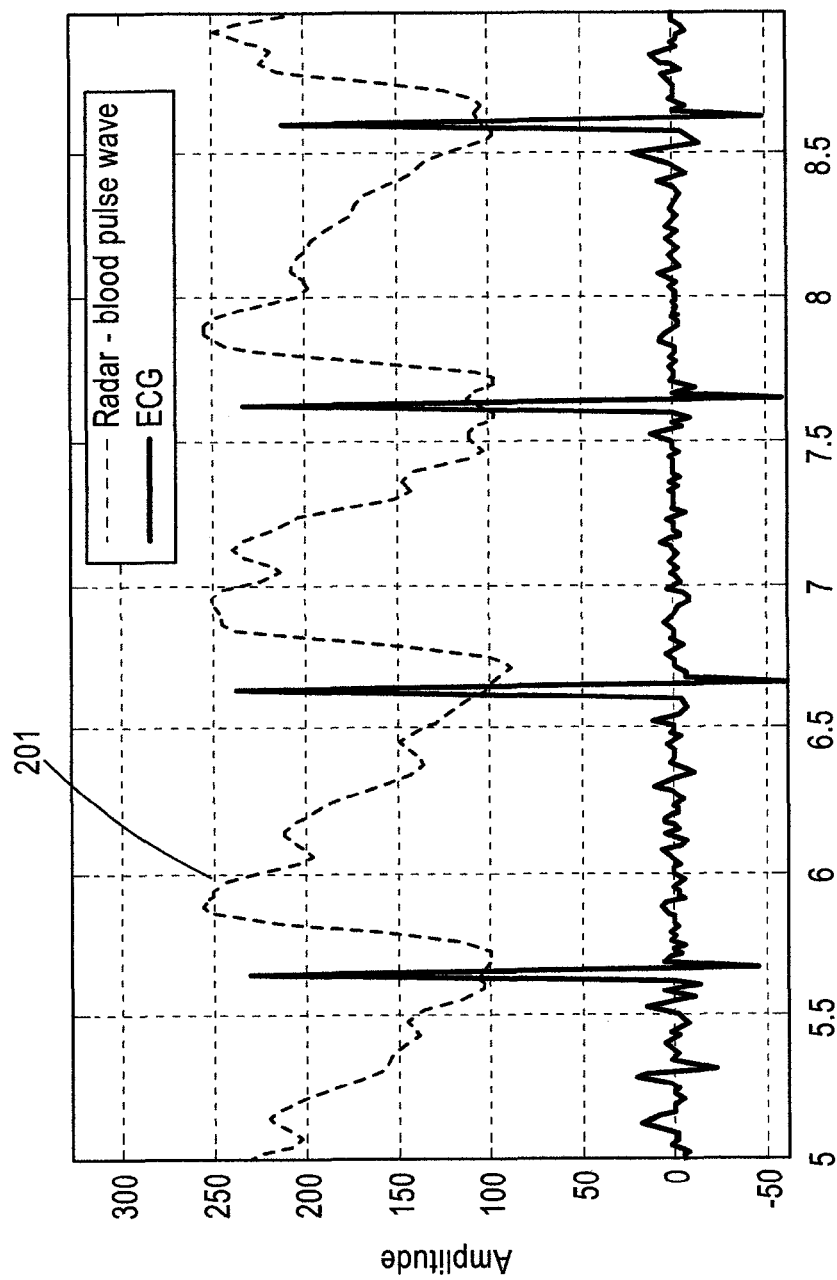
FIG. 2 shows a diagram depicting an example arterial pulse waveform.

In some embodiments, the RF sensor can be utilized to obtain the arterial pulse waveform, which may provide clinical information such as, but not limited to, arterial stiffness, PWV, cardiac output, cNIBP measurements, and the like. For example, the sensor may scan the cross section of objects in its view, which may include an artery. As such, as the pulse wave is propagating through the artery, the RF sensor may measure the changing radar cross section of the artery. In such instances, the changing arterial cross section is related to the pulse wave, and accordingly the arterial pulse waveform maybe determined from the changing cross section. An example arterial pulse wave 201 obtained using this method is depicted in FIG. 2. This method has several advantages in that in obtaining the arterial pulse waveform, it is at least non-invasive, allows penetration into the body, and/or can be operated with little or no expertise.

Figure 3:
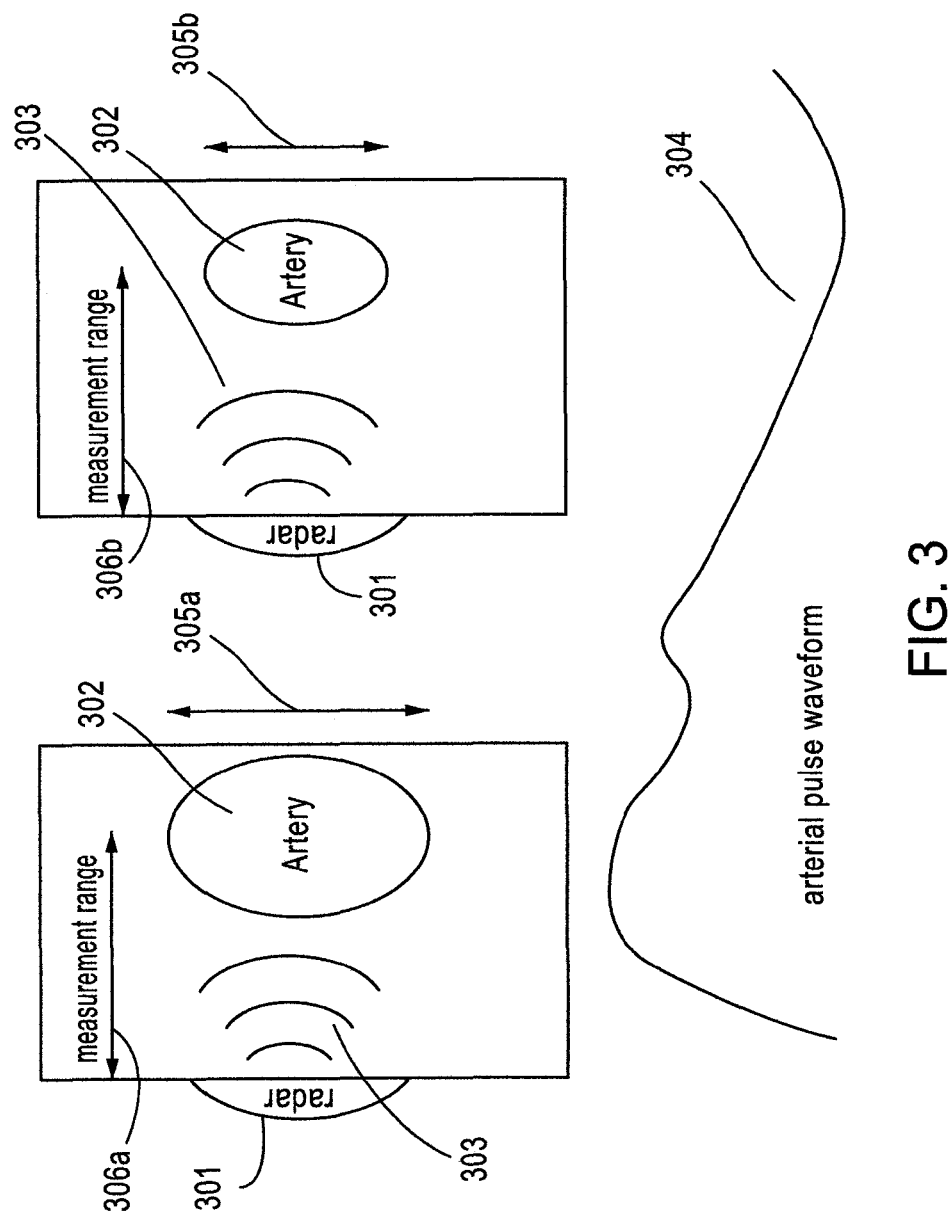
FIG. 3 shows the measurement of arterial pulse waveform from a changing (e.g., time-varying) radar cross section of an artery during cardiac pressure cycle.

FIG. 3 shows the measurement of arterial pulse waveform from a changing (e.g., time-varying) RCS of an artery during cardiac pressure cycle, according to some embodiments. For example, during a cardiac cycle, an RF radar sensor 301 may generate and transmit RF waves 303 towards an artery 302 which may be located at a certain depth from the RF sensor 301 corresponding to a measurement range 306a. In some embodiments, some or all of the transmitted waves 303 may be reflected back to the RF sensor 301. In some instances, the RF sensor 301 may transmit the RF waves 303 continuously or non-continuously. During the cardiac cycle, the diameter of the artery 302 may be varying over time, e.g., 305a and 305b, and as a result the RCS of the artery 302 obtained by the RF sensor 301 changes over time as well. From the measurements of the varying RCS, in some implementations, an arterial pulse waveform 304 representing the pulse wave propagating through the artery may be determined. In turn, from the arterial pulse waveform 304, a variety of clinical information such as but not limited to arterial stiffness, PWV, cardiac output, blood pressure measurements (continuous or non-continuous) may be obtained. In some embodiments, the reflected echo may be modulated by the artery over the course of the cardiac cycle, and information from the reflected echo can be used to determine/estimate the arterial pulse waveform 304. For example, the measurement range 306a may change over the course of the cardiac cycle (e.g., 306a and 306b), leading to changes in the phase of the reflected waves. In such instances, such information can be utilized to determine/estimate the arterial pulse waveform 304.

Usage of RF Waves for Determining PAT

In some embodiments, RF waves may be used to determine the PAT. As discussed above, the ECG signals represent the activation of the ventricles, i.e., the onset of the pulse wave. As such, a determination of the arrival of the pulse at a location on an artery may allow for an estimation/determination of the PAT by comparing the ECG signals with time of arrival for the pulse. In some embodiments, the location may be at a peripheral artery (e.g., fingers, ear lobes, etc.). In some embodiments, the location may be at a depth inside a body, which as discussed above is one advantage of using RF signals. For example, the RF sensor can be located in a variety of places on the body, which allows for the ability of the RF waves to penetrate into a particular depth into the body. In some embodiments, this may allow for choosing an artery for observation (i.e., not necessarily in the finger or earlobe). The RF reflections may be used to identify the time of arrival of the pulse wave to the chosen artery, and the PAT may be determined from the time difference between the ECG R-peak and the RF signal pulse arrival time.

Usage of Two RF Sensors for Determining PTT

Figure 4:
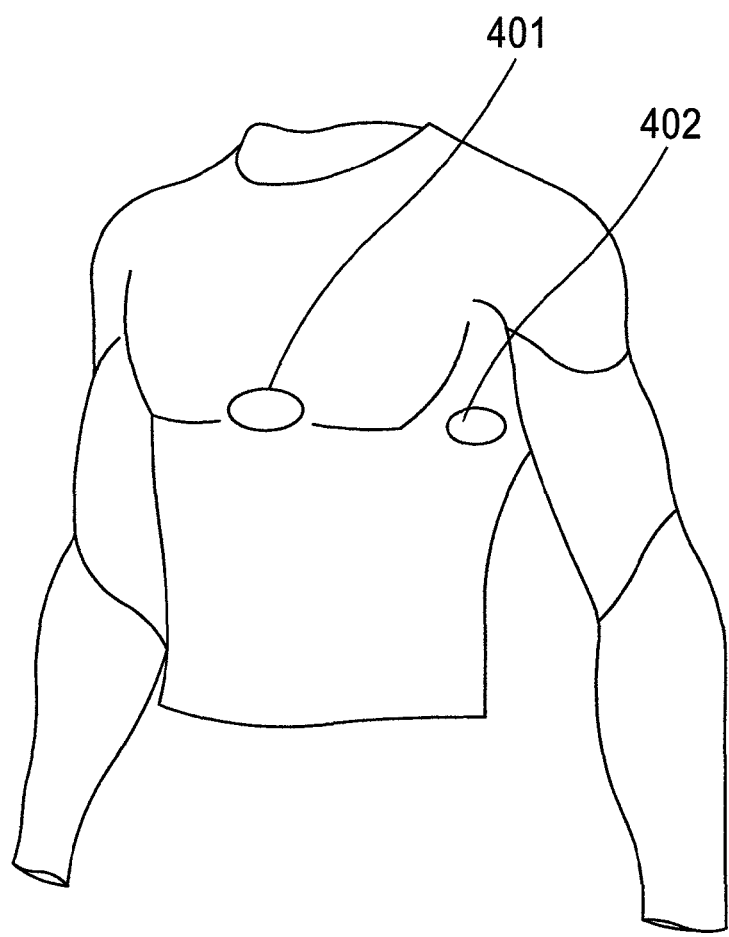
FIG. 4 illustrates an example placement of radio-frequency sensors over the thorax.

In some embodiments, the PTT of the pulse can be determined if the times of arrival of the pulse at two distinct locations can be measured. This follows because the PEP values of the pulse that originated at the same ventricle but arrived at the two different locations is the same, and accordingly, the difference in PAT for the two locations is the same as the difference in PTT of the pulse to the two distinct locations. For example, FIG. 4 shows two RF sensors 401 and 402 located at different positions on the body (e.g., the sternum and the thorax, two suitable locations along the leg, etc.) can be used to sense the pulse wave going through arteries close to each RF sensor. In some embodiments, the RF sensors may be incorporated into clothing (e.g., stockings, shirts, etc.), chest straps, wrist straps, skin patches, and/or the like.

In some embodiments, for each of the RF sensors, the RF signal may be filtered to isolate the reflections from the relevant depth and to remove reflections from static objects. In such embodiments, the PTT may be determined as the time difference between the pulse wave arrival times as measured by the two RF sensors. It is worth noting that the two RF sensors, in some embodiments, may be synchronized. An example way to achieve synchronization may be by using two ECG sensors, where the R peak can be viewed as the synchronizing marker.

Usage of an RF Sensor and a PPG for Determining PTT

As discussed above, the PTT of the pulse can be determined if the times of arrival of the pulse at two distinct locations can be measured. In the previous embodiments, the two locations were disclosed to be at the peripheries of arteries, for example, at the sternum and the thorax, at two suitable locations along the leg, etc. In other embodiments, both locations may not be on the peripheries of arteries as discussed above. For example, one of them can be at the periphery of an artery, and the other can be at a depth inside the body. For example, two co-located sensors, an RF sensor and a PPG sensor, may detect, respectively, an artery located inside the body and a peripheral artery (e.g., on a finger, ear lobes, etc.). In some embodiments, the RF sensor may be used to penetrate into the body and reflections from a specific depth in the body can be isolated by processing the RF echoes. The PPG sensor (e.g., used in reflective mode) may be used to measure reflections from superficial arteries, and the pulse wave of these arteries may then be measured by the PPG. Since the types of observed arteries have a different path from the heart, in some implementations, they therefore may include a different travel time. In some embodiments, this difference can be indicative of the blood pressure. For example, the sensors can be located on the thorax, where reflected RF echoes from the lungs (for example) can be isolated, and pulse waves from arteries going through the lung may be measured in this way. According to some embodiments, the pulse waves from the RF sensor and from the PPG are compared, with the time delay between them determined to be Time Delay=(PTT from the heart to the lung arteries)−(PTT from the heart to the thorax superficial arteries). As disclosed above, this time difference can be used to determine the blood pressure.

Usage of a Single RF Sensor for Determining PTT

In some embodiments, the determination of the PTT of a pulse may be accomplished by a single RF sensor if the times of arrival of the pulse at two distinct locations can be measured using the single sensor. Above, example embodiments have been disclosed where the two distinct locations are at peripheries of arteries, and other embodiments where one location is at a periphery of artery and the other at a depth inside the body. In some embodiments, the two locations may be inside the body at different depths. For example, the single RF sensor may be located in a position where it receives signals for deciphering different arteries at different depths in the body. For example, the sensor may detect pulse waves arriving at different arteries belonging to different branches at different depths in an arterial tree. In such embodiments, the sensor may measure their arrival times at the different depths, and determine/estimate the PTT from the time difference between the arrival times.

Figure 5:
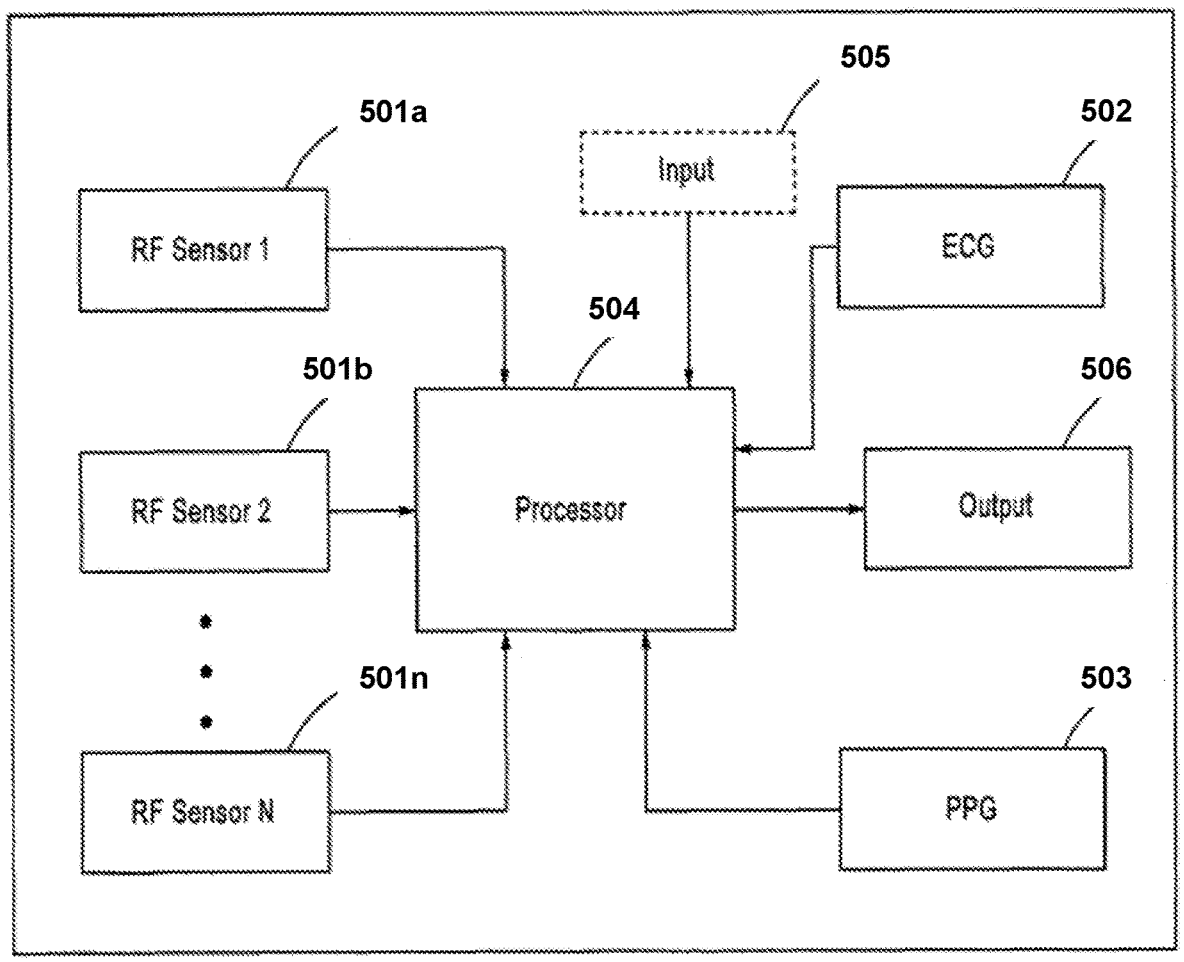
FIG. 5 depicts an example schematic diagram of the components of the apparatus for measuring time-varying radar cross section (RCS) of an artery disclosed herein.

FIG. 5 depicts an example schematic diagram of the components of the apparatus for measuring time-varying radar cross section (RCS) of an artery disclosed herein. For example, the apparatus may comprise one or more RF sensors $501a$, $501b$, $501n$. Further, it may also include an ECG sensor $502$ configured for receiving signals corresponding to an ECG waveform. In some instances, the apparatus may also contain a PPG device $503$. The devices/sensors such as the RF sensors $501a$, $501b$, $501n$, the ECG sensor $502$, the PPG device $503$, etc., may receive signals from the body of a patient (e.g., from arteries). In some embodiments, these sensors/devices may transmit data/information corresponding to the received signals to a processor $504$ configured for executing computer instructions to act on the transmitted data/information. Further, the processor $504$ may receive other input $505$ (e.g., patient data, variables (e.g., temperature, time, etc.), and/or the like), and upon executing computer instructions with some or more of the received input, in some embodiments, the processor $504$ may generate outputs $506$ such as, but not limited to, arterial pulse waveform, blood pressure measurements, etc. These outputs may be presented via any suitable media (e.g., printer, database, display, audio, and the like).

Also, various inventive concepts may be embodied as one or more methods, of which an example has been provided. The acts performed as part of the method may be ordered in any suitable way. Accordingly, embodiments may be constructed in which acts are performed in an order different than illustrated, which may include performing some acts simultaneously, even though shown as sequential acts in illustrative embodiments.

At least some of the embodiments disclosed above, in particular at least some of the methods/processes disclosed, may be realized in circuitry, computer hardware, firmware, software, and combinations thereof (e.g., a computer system). Such computing systems, may include PCs (which may include one or more peripherals well known in the art), smartphones, specifically designed medical apparatuses/devices and/or other mobile/portable apparatuses/devices. In some embodiments, the computer systems are configured to include clients and servers. A client and server are generally remote from each other and typically interact through a communication network (e.g., VPN, Internet). The relationship of client and server arises by virtue of computer programs running on the respective computers and having a client-server relationship to each other.

Some embodiments of the disclosure (e.g., methods and processes disclosed above) may be embodied in a computer program(s)/instructions executable and/or interpretable on a processor, which may be coupled to other devices (e.g., input devices, and output devices/display) which communicate via wireless or wired connect (for example).

While various inventive embodiments have been described and illustrated herein, those of ordinary skill in the art will readily envision a variety of other means and/or structures for performing the function and/or obtaining the results and/or one or more of the advantages described herein, and each of such variations and/or modifications is deemed to be within the scope of the inventive embodiments described herein. More generally, those skilled in the art will readily appreciate that all parameters, dimensions, materials, and configurations described herein are meant to be an example and that the actual parameters, dimensions, materials, and/or configurations will depend upon the specific application or applications for which the inventive teachings is/are used. Those skilled in the art will recognize, or be able to ascertain using no more than routine experimentation, many equivalents to the specific inventive embodiments described herein. It is, therefore, to be understood that the foregoing embodiments are presented by way of example only and that, within the scope of the appended claims and equivalents thereto, inventive embodiments may be practiced otherwise than as specifically described and claimed. Inventive embodiments of the present disclosure are directed to each individual feature, system, article, material, kit, and/or method described herein. In addition, any combination of two or more such features, systems, articles, materials, kits, and/or methods, if such features, systems, articles, materials, kits, and/or methods are not mutually inconsistent, is included within the inventive scope of the present disclosure. Still other embodiments of the present disclosure are patentable over prior art references for expressly lacking one or more features disclosed in the prior art (i.e., claims covering such embodiments may include negative limitations).

Any and all references to publications or other documents, including but not limited to, patents, patent applications, articles, webpages, books, etc., presented anywhere in the present application, are herein incorporated by reference in their entirety. One or more features and/or embodiments disclosed in one or more of incorporated by reference documents herein can also be combined with one or more features/embodiments of the present disclosure to yield yet further embodiments (of the present disclosure).

Moreover, all definitions, as defined and used herein, should be understood to control over dictionary definitions, definitions in documents incorporated by reference, and/or ordinary meanings of the defined terms.

The indefinite articles "a" and "an," as used herein in the specification and in the claims, unless clearly indicated to the contrary, should be understood to mean "at least one."

The phrase "and/or," as used herein in the specification and in the claims, should be understood to mean "either or both" of the elements so conjoined, i.e., elements that are conjunctively present in some cases and disjunctively present in other cases. Multiple elements listed with "and/or" should be construed in the same fashion, i.e., "one or more" of the elements so conjoined. Other elements may optionally be present other than the elements specifically identified by the "and/or" clause, whether related or unrelated to those elements specifically identified. Thus, as a non-limiting example, a reference to "A and/or B", when used in conjunction with open-ended language such as "comprising" can refer, in one embodiment, to A only (optionally including elements other than B); in another embodiment, to B only (optionally including elements other than A); in yet another embodiment, to both A and B (optionally including other elements); etc.

As used herein in the specification and in the claims, "or" should be understood to have the same meaning as "and/or" as defined above. For example, when separating items in a list, "or" or "and/or" shall be interpreted as being inclusive, i.e., the inclusion of at least one, but also including more than one, of a number or list of elements, and, optionally, additional unlisted items. Only terms clearly indicated to the contrary, such as "only one of" or "exactly one of," or, when used in the claims, "consisting of," will refer to the inclusion of exactly one element of a number or list of elements. In general, the term "or" as used herein shall only be interpreted as indicating exclusive alternatives (i.e. "one or the other but not both") when preceded by terms of exclusivity, such as "either," "one of," "only one of," or "exactly one of." "Consisting essentially of," when used in the claims, shall have its ordinary meaning as used in the field of patent law.

As used herein in the specification and in the claims, the phrase "at least one," in reference to a list of one or more elements, should be understood to mean at least one element selected from any one or more of the elements in the list of elements, but not necessarily including at least one of each and every element specifically listed within the list of elements and not excluding any combinations of elements in the list of elements. This definition also allows that elements may optionally be present other than the elements specifically identified within the list of elements to which the phrase "at least one" refers, whether related or unrelated to those elements specifically identified. Thus, as a non-limiting example, "at least one of A and B" (or, equivalently, "at least one of A or B," or, equivalently "at least one of A and/or B") can refer, in one embodiment, to at least one, optionally including more than one, A, with no B present (and optionally including elements other than B); in another embodiment, to at least one, optionally including more than one, B, with no A present (and optionally including elements other than A); in yet another embodiment, to at least one, optionally including more than one, A, and at least one, optionally including more than one, B (and optionally including other elements); etc.

In the claims, as well as in the specification above, all transitional phrases such as "comprising," "including," "carrying," "having," "containing," "involving," "holding," "composed of," and the like are to be understood to be open-ended, i.e., to mean including but not limited to. Only the transitional phrases "consisting of" and "consisting essentially of" shall be closed or semi-closed transitional phrases, respectively, as set forth in the United States Patent Office Manual of Patent Examining Procedures, Section 2111.03.

What is currently claimed is:

1. A continuous blood pressure measuring apparatus for measuring time-varying radar cross section (RCS) of an artery of a patient so as to determine blood pressure of the patient, comprising:
    a radio-frequency (RF) transceiver for generating RF waves;
    at least one RF sensor configured for positioning on or adjacent the skin of a patient, and continuously transmit the RF waves into tissue of the patient and continuously receiving RF wave reflections from at least one artery located within the tissue;
    at least one ECG sensor configured for:
        positioning on the patient's body, and
        continuously receiving ECG signals corresponding to an ECG waveform of the patient, and
    a processor having computer instructions operating thereon configured to cause the processor to continuously:
        determine an RF arterial pulse waveform based on the received RF wave reflections, wherein the time-varying radar cross section (RCS) comprises the RF arterial pulse waveform,
        correlate the time-varying RCS to a time-varying diameter of the at least one artery,
        synchronize the ECG signals with the RF wave reflections from the at least one artery located within the tissue,
        determine, based on the time-varying RCS and the synchronization, a pre-ejection period (PEP) indicating a time lapse between a ventricular polarization as indicated by the ECG signals and an opening of aortic value of the patient as indicated by the time-varying RCS, and
        determine values of systolic blood pressure (SBP) and diastolic blood pressure (DBP), based on:
            the time-varying RCS, and
            the PEP, the PEP having been determined on the time-varying RCS and the synchronization.

2. The apparatus of claim 1, wherein the at least one RF sensor comprises at least one antennae, and/or the at least one RF sensor is configured with flexibility to enable the at least one RF sensor to conform to the skin of the patient.

3. The apparatus of claim 1, wherein the computer instructions are additionally configured to cause the processor to condition the RF arterial pulse waveform using at least one radar echo from a specific range.

4. The apparatus of claim 1, wherein the computer instructions are additionally configured to cause the processor to condition the RF arterial pulse waveform using band pass filtering.

5. The apparatus of claim 1, wherein the computer instructions are additionally configured to cause the processor to characterize the RF arterial pulse waveform including one or more characteristics selected from the group consisting of:
 a peak-to-peak amplitude of the RF arterial pulse waveform,
 a time location of at least one of a peak of the RF arterial pulse waveform,
 a first derivative peak, and one or more additional points marking an RF-arterial-pulse-arrive-time (RF-PAT), and
 a timing of a dicrotic notch of the RF arterial pulse waveform.

6. The apparatus of claim 1, wherein
 the at least one RF sensor is positioned to receive the RF wave reflections from the aorta of the patient, and
 the computer instructions are additionally configured to cause the processor to determine an R-peak of the ECG waveform.

7. The apparatus of claim 1, wherein the computer instructions are additionally configured to cause the processor to determine an arterial-pulse-travel-time (PTT) by subtracting the PEP from PAT.

8. The apparatus of claim 7, wherein the SBP and the DBP are determined based on the PTT and calibrated for each patient.

9. The apparatus of 8, wherein calibration comprises determining coefficients corresponding to determining the SBP and the DBP.

10. The apparatus of claim 1, wherein the at least one RF sensor is configured for sensing the RF wave reflections corresponding to an arterial-pulse-arrival-time (PAT) to each of two different arterial tree locations, the two different arterial tree locations discerned based on depth resolution of the tissue.

11. The apparatus of claim 1, wherein the at least one RF sensor is configured for sensing the RF wave reflections corresponding to an arterial-pulse-arrival-time (PAT) to each of two different arterial tree locations, wherein the computer instructions are additionally configured to cause the processor to determine an arterial-pulse-travel-time (PTT) by determining a difference between the PAT at the two different arterial tree locations.

12. The apparatus of claim 1, wherein the computer instructions are additionally configured to cause the processor to determine an arterial pulse-wave velocity (PWV), wherein the PWV equals a propagation distance of the arterial pulse wave divided by pulse travel time (PTT).

13. The apparatus of claim 1, wherein the computer instructions are further configured to cause the processor to synchronize the ECG signals with the RF wave reflections from the at least one artery located within the tissue based at least in part on a timing associated with one or more R peaks in the ECG signals.

14. The apparatus of claim 1, wherein the computer instructions are additionally configured to cause the processor to determine a pulse-arrival-time (PAT) based on a time difference between an RF-arterial-pulse-arrive-time (RF-PAT) and an R-peak of the ECG waveform.

15. The apparatus of claim 1, wherein the computer instructions are additionally configured to cause the processor to output the SBP and DBP.

16. A continuous blood pressure measuring method for measuring a time-varying radar cross section (RCS) of at least one an artery within a tissue of a patient so as to determine blood pressure of the patient, comprising:
 positioning at least one ECG sensor and at least one RF sensor on the patient's body, and
 continuously:
  transmitting RF waves into the tissue at a first location via the at least one RF sensor;
  receiving RF wave reflections from the at least one artery via at least one RF sensor;
  receiving ECG signals corresponding to an ECG waveform of the patient via the at least one ECG sensor,
  synchronizing the ECG signals with the RF wave reflections from the at least one artery located within the tissue; and
  determining an RF arterial pulse waveform based on the received RF wave reflections, wherein the RF arterial pulse waveform corresponds to the time-varying (RCS) of the at least one artery;
  determining, based on the time-varying RCS and the synchronization, a pre-ejection period (PEP) indicating a time lapse between a ventricular polarization as indicated by the ECG signals and an opening of aortic value of the patient as indicated by the time-varying RCS,
  conditioning the RF arterial pulse waveform using at least one radar echo from a specific range adapted to the at least one artery; and
  determining values of systolic blood pressure (SBP) and diastolic blood pressure (DBP), based on:
   the time varying RCS, and
   the PEP, the PEP having been determined on the time-varying RCS and the synchronization.

17. The method of claim 16, wherein the at least one RF sensor comprises a first RF sensor and a second RF sensor, the method further comprising:
 sensing, via the first RF sensor, RF wave reflections corresponding to an arterial-pulse-arrival-time (PAT) at a first arterial tree location,
 sensing, via the second RF sensor, signals corresponding to PAT at a second arterial tree location,
 determining the PAT at each location, and
 determining the difference between the PAT at the two locations so as to determine the an arterial-pulse-travel-time (PTT).

18. The method of claim 17, further comprising determining a timing of a dicrotic notch of the RF arterial pulse waveform.

19. The method of claim 16, further comprising determining a timing of a dicrotic notch of the RF arterial pulse waveform.

20. The method of claim 16, wherein synchronizing the ECG signals with the RF wave reflections from the at least one artery located within the tissue is based at least in part on a timing associated with one or more R peaks in the ECG signals.

21. The method of claim 16, further comprising determining a pulse-arrival-time (PAT) based on a time difference between an RF-arterial-pulse-arrive-time (RF-PAT) and an R-peak of the ECG waveform.

22. The method of claim 16, further comprising outputting the SBP and DBP.

23. The method of claim 16, further comprising determining an arterial-pulse-travel-time (PTT) by subtracting the PEP from PAT.

24. The method of claim 23, wherein the SBP and the DBP are determined based on the PTT and calibrated for each patient.

25. The method of 24, wherein calibration comprises determining coefficients corresponding to each of the SBP and the DBP.

* * * * *